US008329933B2

(12) United States Patent
Mayorga et al.

(10) Patent No.: US 8,329,933 B2
(45) Date of Patent: Dec. 11, 2012

(54) LOW-IMPURITY ORGANOSILICON PRODUCT AS PRECURSOR FOR CVD

(75) Inventors: Steven Gerard Mayorga, Oceanside, CA (US); Mark Leonard O'Neill, San Marcos, CA (US); Kelly Ann Chandler, San Marcos, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 13/205,015

(22) Filed: Aug. 8, 2011

(65) Prior Publication Data

US 2011/0295033 A1 Dec. 1, 2011

Related U.S. Application Data

(62) Division of application No. 11/753,153, filed on May 24, 2007, now abandoned.

(60) Provisional application No. 60/813,087, filed on Jun. 13, 2006.

(51) Int. Cl.
*C07F 7/04* (2006.01)

(52) U.S. Cl. ........ 556/470; 556/442; 556/466; 556/467; 556/471

(58) Field of Classification Search .................. 556/442, 556/466, 467, 470, 471
See application file for complete search history.

(56) References Cited

U.S. PATENT DOCUMENTS

| 5,084,588 A | 1/1992 | Ocheltree et al. |
| 5,210,254 A | 5/1993 | Ritscher et al. |
| 5,698,726 A | 12/1997 | Rauleder et al. |
| 6,054,379 A | 4/2000 | Yau et al. |
| 6,100,418 A | 8/2000 | Standke et al. |
| 6,150,552 A | 11/2000 | Schreier et al. |
| 6,242,628 B1 | 6/2001 | Kropfgans et al. |
| 6,583,048 B1 | 6/2003 | Vincent et al. |
| 2002/0002299 A1 | 1/2002 | Arkles et al. |
| 2004/0241463 A1 | 12/2004 | Vincent et al. |
| 2005/0038276 A1 | 2/2005 | Laxman et al. |
| 2005/0059835 A1 | 3/2005 | Wassmann-Wilken et al. |
| 2008/0188679 A1 | 8/2008 | Mayorga et al. |

FOREIGN PATENT DOCUMENTS

| CN | 1576390 A | 2/2005 |
| EP | 0 741 137 A1 | 11/1996 |
| EP | 0741137 B1 | 1/2001 |
| JP | 63-046269 | 2/1988 |
| JP | 02-235887 | 9/1990 |
| JP | 04230291 | 12/1990 |
| JP | 04-117391 | 4/1992 |
| WO | 8703071 | 5/1987 |
| WO | 2004/100926 A2 | 11/2004 |

OTHER PUBLICATIONS

Tacks, R., et al; Ester des (Hydroxymethyl) [(Trimethylslyl) Methyl] Silans: Synthese und Thermisch Induzierte Umlagerung; Journal of Organometallic Chemistry, vol. 354; 1988; pp. 139-146.

*Primary Examiner* — Shailendra Kumar
(74) *Attorney, Agent, or Firm* — Joseph D. Rossi

(57) ABSTRACT

The present invention provides an organosilicon composition comprising diethoxymethylsilane, a concentration of dissolved residual chloride, and a concentration of dissolved residual chloride scavenger that does not yield unwanted chloride salt precipitate when combined with another composition comprising diethoxymethylsilane.

14 Claims, 4 Drawing Sheets

LOW-IMPURITY ORGANOSILICON PRODUCT AS PRECURSOR FOR CVD

This application is a divisional patent application of U.S. patent application Ser. No. 11/753,153, filed on May 24, 2007, now abandoned, the disclosure of which is incorporated herein by reference in its entirety. This application also claims the benefit of priority under 35 U.S.C. §119(e) to earlier filed U.S. patent application Ser. No. 60/813,087, filed on Jun. 13, 2006, the disclosure of which is incorporated herein by reference in its entirety.

BACKGROUND OF THE INVENTION

The present invention is related to the field of low dielectric constant materials prepared by chemical vapor deposition (CVD) methods which serve as insulating layers in electronic devices. In particular, the present invention is directed to compositions for use as precursors to the low dielectric constant materials that have predetermined concentration limitations of certain impurities to eliminate process problems related to precipitation of such impurities.

The electronics industry utilizes dielectric materials as insulating layers between circuits and components of integrated circuits (IC) and associated electronic devices. Line dimensions must be reduced in order to increase the speed and memory storage capability of microelectronic devices (e.g., computer chips). As the line dimensions decrease, the insulating requirements for the interlayer dielectric (ILD) become more rigorous. Shrinking dimensions requires a lower dielectric constant to minimize the RC time constant, where R is the resistance of the conductive line and C is the capacitance of the insulating dielectric layer. C is inversely proportional to spacing and proportional to the dielectric constant (k) of the ILD.

Conventional silica ($SiO_2$) CVD dielectric films produced from $SiH_4$ or TEOS (tetraethylorthosilicate) and oxygen have a dielectric constant (k) of greater than 4.0. There are several ways in which the industry has attempted to produce silica-based CVD films with lower dielectric constants, the most successful being the doping of the insulating film with carbon atoms, fluorine atoms, or organic groups containing carbon and fluorine. Doping the silica with carbon atoms or organic groups lowers the k of the resulting dielectric film for several reasons. Organic groups, such as methyl, are hydrophobic; thus, adding methyl or other organic groups to the composition can act to protect the resulting CVD deposited film from contamination with moisture. The incorporation of such organic groups also serves to "open up" the structure of the silica, possibly leading to lower density through space-filling with bulky $CH_x$ bonds. Organic groups are also useful because some functionalities can be incorporated into the organosilicate glass (OSG), then subsequently "burned out" or oxidized to produce a more porous material which will inherently have a lower dielectric constant.

Carbon can be incorporated into an ILD by using an organosilane as the silicon source material in the PECVD reaction. An example of such would be the use of methylsilanes, $(CH_3)_xSiH_{(4-x)}$, as disclosed in U.S. Pat. No. 6,054,379. Alkoxysilanes (also referred to herein as silyl ethers) have also been disclosed as effective precursors for the introduction of organic moieties into the ILD. Particularly useful alkoxysilanes are disclosed in U.S. Pat. No. 6,583,048. Of such alkoxysilanes, diethoxymethylsilane (DEMS) has found significant commercial use.

The manufacture of organosilanes or alkoxysilanes, however, typically requires the use of halosilane chemical staring materials such as, for example, chlorosilane or organochlorosilane. In such reactions, the alkoxy group replaces the halogen, forming the desired alkoxysilane. Dimethyldimethoxysilane (DMDMOS), for example, is commercially manufactured utilizing the chemical reaction of dimethyldichlorosilane with methanol as shown below:

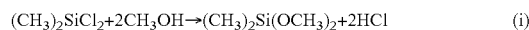

(i)

In a similar manner, DEMS is typically prepared primarily by one of two synthetic routes: the "direct" synthesis, shown below by equation (ii), involving the reaction of dichloromethylsilane with ethanol; and the "orthoformate" synthesis, shown by equation (iii), which involves the reaction of dichloromethylsilane with triethylorthoformate:

(ii)

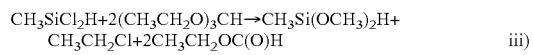

(iii)

In all of the above cases the synthesis of the desired alkoxysilane is accompanied by the production of stoichiometric quantities of chloride-containing byproducts such as hydrochloric acid (HCl), as in the case of the reactions (i) and (ii), or ethylchloride, ($CH_3CH_2Cl$) as in the case of the latter reaction. The crude product mixture also typically contains some amount of unconverted chloromethylsilane. This is particularly true for the synthesis of DEMS, in which it is not practical to treat the dichloromethylsilane starting material with a substantial molar excess of reactant in order to drive the reaction to quantitative conversion. The presence of Si—H in the dichloromethylsilane makes it particularly vulnerable to attack forming undesirable side-reaction products if exposed to a substantial excess of either ethanol ($CH_3CH_2OH$) or triethylorthoformate ($(CH_3CH_2O)_3CH$). Given these constraints, the crude DEMS product typically has a significant amount of acid chlorides (HCl) and/or complexed silicon chloride impurities. Distillation is effective for removing most of the chloride impurities, but has limited efficacy for reducing the chlorides to the low levels required for CVD precursor source chemicals (e.g., <10 ppm by weight). In order to achieve these low chloride levels the product can be treated with a basic scavenger which will remove the chloride through complexation or adsorption. The basic scavenger can be in the form of a pure liquid or solid, such as in the case of an organoamine, in the form of a resin material such as in a packed bed of solid adsorbent material, or in the form of a gas such as, for example, gaseous ammonia.

Industry standards for ILD source materials have stringent requirements for low levels of residual chloride and nitrogen-containing components. Residual chloride presents integration issues due to its potential migration and high reactivity. Nitrogen also needs to be minimized because of its potential for diffusion, possibly causing resist poisoning issues. Consequently, unacceptably high levels of halogen or nitrogen in CVD feed materials may cause undesirable performance problems for the resulting ILD films.

As described above, two common routes for the preparation of DEMS are exemplified, each of which may yield unacceptably high levels of chloride contamination in the crude product due to unreacted starting material, acid chloride or complexed chloride byproducts. Distillation is commonly employed to purify the crude product, but it is not an effective means for reducing the chloride to acceptable levels. Typically, the distilled DEMS product is treated with an appropriate amount of a halide scavenger material in order to complex the chloride as the corresponding insoluble salt. This halide scavenger is often basic in nature, examples of which include amines, imides, alkali metal alcoholates, metal alkoxides, or solid adsorbent or resin materials such as activated carbons, alkali-treated activated carbons or other base-treated adsorbent substrates. The scavenger-chloride salt, thus formed, can be separated by conventional means such as filtration or further distillation in order to produce a DEMS product with less than 10 ppm chloride by weight.

There are significant drawbacks, however, associated with the use of residual chloride scavengers. For example, during CVD processing it is not uncommon that different lots of organosilicon precursor such as, for example, DEMS, may be combined, such as when a partially empty container is backfilled with a second source container of precursor, or when two different precursor source containers are feeding a common manifold. Precipitation of solids may occur if a sample of precursor containing a substantial amount of dissolved residual chloride is combined with a second source of precursor containing a substantial amount of dissolved residual basic scavenger. Solids formation in this manner leads to production problems because the solid precipitate typically restricts or blocks the flow of the liquid precursor, contaminates the liquid delivery or deposition hardware, and numerous potential performance and or quality issues associated with the deposited low-k films. Accordingly, there is a need in the art for an organosilicon precursor composition that is substantially free of having the potential to precipitate chloride salts upon mixture with other organosilicon precursor material.

BRIEF SUMMARY OF THE INVENTION

The present invention satisfies the need for an organosilicon precursor composition that is substantially free of having the potential to precipitate chloride salts upon mixture with other organosilicon precursor material. The present invention satisfies this need by defining an upper limit for the concentration of chloride and chloride scavenger in an organosilicon such as, for example, DEMS, that must be met in order to ensure that chloride will not precipitate when such organosilicon product is mixed either with another lot of the product from the same source or with another product from a different source.

In one aspect, the present invention provides a method for preventing solids formation in an organosilicon material employed in a chemical vapor deposition process, the method comprising the steps of: providing an organosilicon composition comprising: at least one organosilicon selected from the group consisting of: an alkoxysilane and a carboxysilane; a first concentration of dissolved residual chloride; and a first concentration of dissolved residual chloride scavenger, wherein the organosilicon composition has a first $K_{sp}(os)$ defined as the product of [the first concentration of the dissolved residual chloride in parts per million by weight]$^X$, wherein X is 1, 2, 3, or 4 and [the first concentration of the dissolved residual chloride scavenger in parts per million by weight], wherein the first concentration of dissolved residual chloride is less than the square root of the first $K_{sp}(os)$ when X is 1, less than cubed root of the first $K_{sp}(os)$ when X is 2, less than the fourth root of the first $K_{sp}(os)$ when X is 3, or less than the fifth root of the first $K_{sp}(os)$ when X is 4, and the first concentration of the dissolved residual chloride scavenger is less than the square root of the first $K_{sp}(os)$ when X is 1, less than cubed root of the first $K_{sp}(os)$ when X is 2, less than the fourth root of the first $K_{sp}(os)$ when X is 3, or less than the fifth root of the first $K_{sp}(os)$ when X is 4; providing a second organosilicon comprising at least one organosilicon selected from the group consisting of: an alkoxysilane and a carboxysilane, a second concentration of dissolved residual chloride, and a second concentration of dissolved residual chloride scavenger, wherein the second organosilicon has a second $K_{sp}(os)$ defined as the product of [the second concentration of the dissolved residual chloride in parts per million by weight]$^X$, wherein X is 1, 2, 3, or 4, and [the second concentration of the dissolved residual chloride scavenger in parts per million by weight] and wherein each of the second concentration of dissolved residual chloride and the second concentration of the dissolved residual chloride scavenger is less than the square root of the first $K_{sp}(os)$ when X is 1, less than cubed root of the first $K_{sp}(os)$ when X is 2, less than the fourth root of the first $K_{sp}(os)$ when X is 3, or less than the fifth root of the first $K_{sp}(os)$ when X is 4.

In preferred embodiments of the present invention, the organosilicon composition comprises diethoxymethylsilane (DEMS).

DETAILED DESCRIPTION OF THE INVENTION

The present invention provides an organosilicon composition comprising: at least one organosilicon selected from the group consisting of: an alkoxysilane and a carboxysilane; a first concentration of dissolved residual chloride; and a first concentration of dissolved residual chloride scavenger, wherein the organosilicon composition has a first $K_{sp}(os)$ defined as the product of [the first concentration of the dissolved residual chloride in parts per million by weight]$^X$, wherein X is 1, 2, 3, or 4 and [the first concentration of the dissolved residual chloride scavenger in parts per million by weight], wherein the first concentration of dissolved residual chloride is less than the square root of the first $K_{sp}(os)$ when X is 1, less than cubed root of the first $K_{sp}(os)$ when X is 2, less than the fourth root of the first $K_{sp}(os)$ when X is 3, or less than the fifth root of the first $K_{sp}(os)$ when X is 4, and the first concentration of the dissolved residual chloride scavenger is less than the square root of the first $K_{sp}(os)$ when X is 1, less than cubed root of the first $K_{sp}(os)$ when X is 2, less than the fourth root of the first $K_{sp}(os)$ when X is 3, or less than the fifth root of the first $K_{sp}(os)$ when X is 4.

Figure 1:
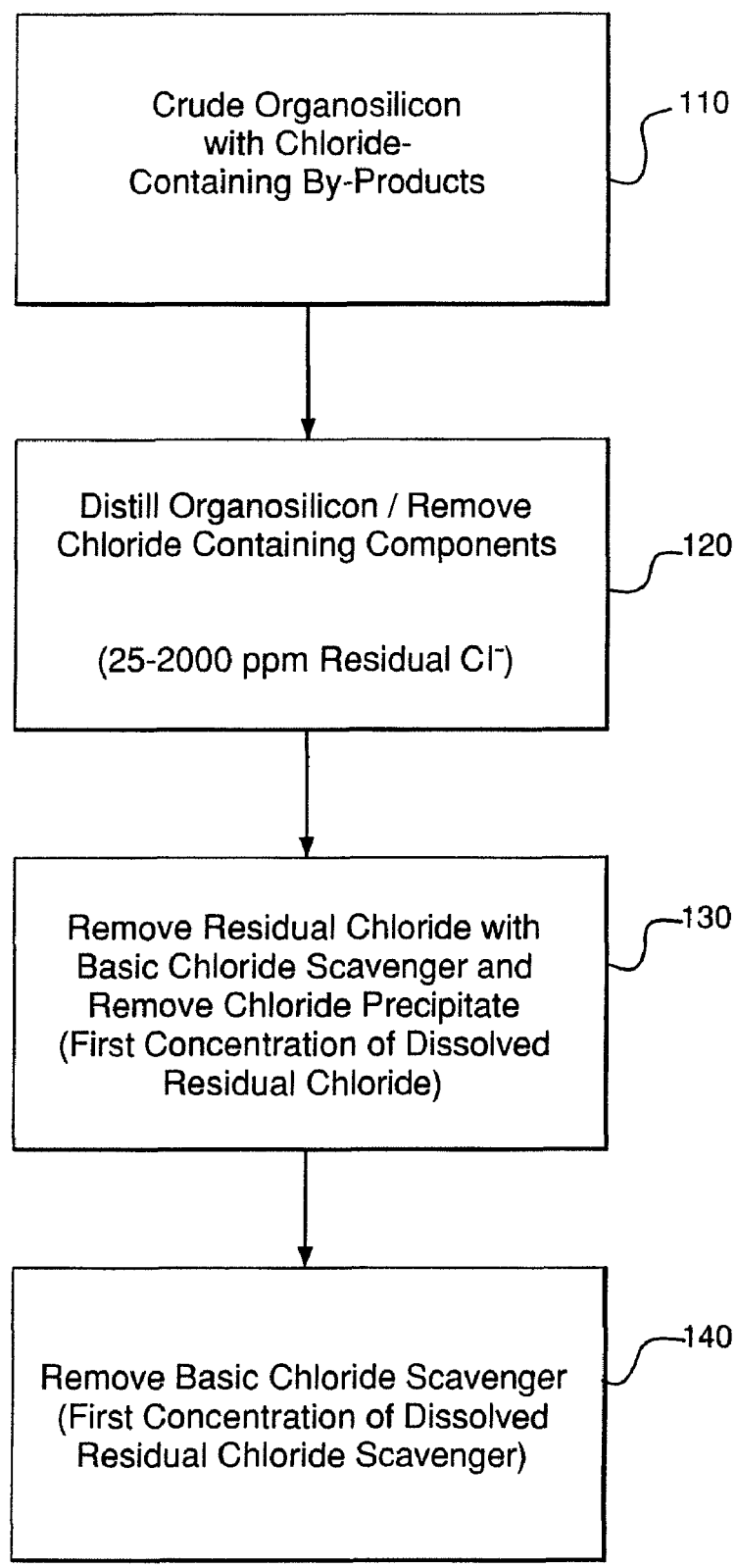
FIG. 1 is a flow diagram illustrating the present invention.

FIG. 1 illustrates an exemplary process that can be employed to obtain the compositions of the present invention. Referring to FIG. 1, step 110 represents the manufacture of "crude" a organosilicon composition, i.e., organosilicon compositions whose manufacture is typically accompanied by stoichiometric quantities of chloride-containing byproducts that need to be removed to purify the organosilicon product prior to its intended use. The organosilicon compositions according to the present invention are typically employed as organosilicon precursors for use in making interlayer dielectric (ILD) films having a dielectric constant of 3.5 or less and, preferably, 3 or less, by chemical vapor deposition (CVD) such as, for example, plasma enhanced CVD (PECVD) or thermal CVD. Preferred orgaonosilicons according to the present invention include at least one selected from the group consisting of alkoxysilanes and carboxysilanes.

In preferred embodiments of the present invention, the alkoxysilane is a compound of the formula $R^1{}_n(R^2O)_{3-n}SiH$ where $R^1$ can be independently H, $C_1$ to $C_{10}$, linear or branched, saturated, singly or multiply unsaturated, cyclic, partially or fully fluorinated; $R^2$ can be independently $C_1$ to $C_{10}$, linear or branched, saturated, singly or multiply unsaturated, cyclic, aromatic, partially or fully fluorinated, n is 0, 1, or 2. Examples of such alkoxysilanes include diethoxymethylsilane, methyldimethoxysilane, dimethoxymethlysilane, di-isopropoxymethylsilane, di-tertiarybutoxymethylsilane, triethoxysilane, dimethylmethoxysilane, dimethylethoxysilane, di-tertiarybutylethoxysilane, and mixtures thereof.

In another preferred embodiment of the present invention, the alkoxysilane is a compound of the formula $R^1{}_n(R^2O)_{2-n}HSi-O-SiHR^3{}_m(OR^4)_{2-m}$ where $R^1$ and $R^3$ can be independently H, $C_1$ to $C_{10}$, linear or branched, saturated, singly or multiply unsaturated, cyclic, partially or fully fluorinated; $R^2$ and $R^4$ can be independently $C_1$ to $C_{10}$, linear or branched, saturated, singly or multiply unsaturated, cyclic, aromatic, partially or fully fluorinated, n is 0 or 1 and m is 0, 1 or 2. 1,3-dimethyl-1,3-diethoxydisiloxane is an example of such alkoxysilane.

In yet another embodiment of the present invention, the alkoxysilane is a compound of the formula $R^1{}_n(R^2O)_{2-n}HSi-SiHR^3{}_m(OR^4)_{2-m}$ where $R^1$ and $R^3$ can be independently H, $C_1$ to $C_{10}$, linear or branched, saturated, singly or multiply unsaturated, cyclic, partially or fully fluorinated, $R^2$ and $R^4$ can be independently $C_1$ to $C_{10}$, linear or branched, saturated, singly or multiply unsaturated, cyclic, aromatic, partially or fully fluorinated, n is 0 or 1 and m is 0, 1 or 2. 1,2-dimethyl-1,2-diethoxydisilane is an example of such alkoxysilane.

In yet another embodiment of the present invention, the alkoxysilane is a compound of the formula $R^1{}_n(R^2O)_{2-m}HSi-R^5-SiHR^3{}_m(OR^4)_{2-m}$ where $R^1$ and $R^3$ can be independently H, $C_1$ to $C_{10}$, linear or branched, saturated, singly or multiply unsaturated, cyclic, partially or fully fluorinated, $R^2$ and $R^4$ can be independently $C_1$ to $C_{10}$, linear or branched, saturated, singly or multiply unsaturated, cyclic, aromatic, partially or fully fluorinated, $R^5$ can be independently $C_1$ to $C_{10}$, linear or branched, saturated, singly or multiply unsaturated, cyclic, partially or fully fluorinated, n is 0 or 1 and m is 0, 1 or 2. Examples include: 1,3-dimethyl-1,3-diethoxydisilamethane and 1,3-diethyl-1,3-diethoxydisilamethane.

Preferred alkoxysilanes are, for example, those disclosed in U.S. Pat. No. 6,583,048, which is incorporated herein by reference in its entirety, as well as alkoxysilane dimers and oligomers. Diethoxymethylsilane is the most preferred alkoxysilane.

Preferred orgaonosilicons according to the present invention also include carboxysilanes. For example, the carboxysilane can be a compound of the formula $R^1{}_n(R^2C(O)O)_{3-n}SiH$ where $R^1$ can be independently H, $C_1$ to $C_{10}$, linear or branched, saturated, singly or multiply unsaturated, cyclic, partially or fully fluorinated; $R^2$ can be independently H, $C_1$ to $C_{10}$, linear or branched, saturated, singly or multiply unsaturated, cyclic, aromatic, partially or fully fluorinated, n is 0, 1, or 2. Methyldiacetoxysilane is an example of such carboxysilane.

In another embodiment of the present invention, the carboxysilane is a compound of the formula $R^1{}_n(R^2C(O)O)_{2-n}HSi-O-SiHR^3{}_m(O(O)CR^4)_{2-m}$ where $R^1$ and $R^3$ can be independently. H, $C_1$ to $C_{10}$, linear or branched, saturated, singly or multiply unsaturated, cyclic, partially or fully fluorinated; $R^2$ and $R^4$ can be independently H, $C_1$ to $C_{10}$, linear or branched, saturated, singly or multiply unsaturated, cyclic, aromatic, partially or fully fluorinated, n is 0 or 1 and m is 0, 1 or 2. 1,3-dimethyl-1,3-diacetoxydisiloxane is an example of such carboxysilane.

In another embodiment of the present invention, the carboxysilane is a compound of the formula $R^1{}_n(R^2C(O)O)_{2-n}HSi-SiHR^3{}_m(O(O)CR^4)_{2-m}$ where $R^1$ and $R^3$ can be independently H, $C_1$ to $C_{10}$, linear or branched, saturated, singly or multiply unsaturated, cyclic, partially or fully fluorinated; $R^2$ and $R^4$ can be independently H, $C_1$ to $C_{10}$, linear or branched, saturated, singly or multiply unsaturated, cyclic, aromatic, partially or fully fluorinated, n is 0 or 1 and m is 0, 1 or 2. 1,2-dimethyl-1,2-diacetoxydisilane is an example of such carboxysilane.

In yet another embodiment of the present invention, the carboxysilane is a compound of the formula $R^1{}_n(R^2C(O)O)_{2-n}HSi-R^5-SiHR^3{}_m(O(O)CR^4)_{2-m}$ where $R^1$ and $R^3$ can be independently H, $C_1$ to $C_{10}$, linear or branched, saturated, singly or multiply unsaturated, cyclic, partially or fully fluorinated; $R^2$ and $R^4$ can be independently H, $C_1$ to $C_{10}$, linear or branched, saturated, singly or multiply unsaturated, cyclic, aromatic, partially or fully fluorinated, $R^5$ can be independently $C_1$ to $C_{10}$, linear or branched, saturated, singly or multiply unsaturated, cyclic, partially or fully fluorinated, n is 1 to 3, and m is 0, 1 or 2. Examples include 1,3-dimethyl-1,3-dipropionoxydisilamethane and 1,3-diethyl-1,3-diacetoxydisilamethane.

Organosilicon compositions according to the present invention typically comprise a concentration of dissolved residual chloride because, as detailed above, organosilicons such as, for example, alkoxysilanes and carboxysilanes are typically synthesized from chlorosilanes by the reaction with the appropriate alcohol or carboxylic acid, respectively, to form the desired alkoxysilane. This synthetic approach also produces hydrogen chloride as a stoichiometric byproduct. The alkoxysilane or carboxysilane composition is typically purified by removal of chloride-containing components such as, for example, byproducts, HCl, dissolved chloride salts and chloride precipitates from the synthesis process. Although the present invention will be described in connection with the removal of dissolved residual chlorides resulting from the employment of chlorosilane starting chemical materials as described above, it should be understood by the skilled artisan, however, that the use of the present invention has wider applicability to the removal of any dissolved residual halogen-containing byproduct depending upon whether, for example, a bromo, fluoro, or iodosilane is employed as the starting material to manufacture the organosilicon composition.

Referring to step 120 of FIG. 1, the majority of the chloride-containing components can be removed from the crude alkoxysilane or carboxysilane composition through distillation resulting in an alkoxysilane or carboxysilane with 25-2000 ppm chloride by weight. Thus, further processing is typically required to further reduce the dissolved residual chloride to the levels required for use, for example, as a precursor in a chemical vapor deposition process.

Referring to step 130 of FIG. 1, the dissolved residual chloride is further removed to obtain a first concentration of dissolved residual chloride. As used herein, the phrase "a first concentration of dissolved residual chloride" refers to the level of dissolved residual chloride after the further removal step 130 of FIG. 1. The prior art is replete with a variety of purification techniques that employ basic chloride scavengers to further lower the concentration of dissolved residual chloride. One such method is disclosed in EP 282486 A2 and EP 741137 A1 and involves neutralization with alkali metal alcoholates, followed by separation of the resulting salt. The use of ammonia and alcoholates to neutralize excess acid halides is disclosed in U.S. Pat. Nos. 6,150,552 and 6,242,628. Alkali-treated activated carbons and basic ion exchange resins have also been used to remove trace chloride from alkoxysilanes (Chem. Abstracts, Vol. 117 (1992); p. 713, 251554). The use of activated carbons to scavenge residual halogen from alkoxysilane based materials is disclosed in U.S. Pat. No. 6,100,418. Other various approaches to reduce the acid halide content of alkoxysilanes have been disclosed, such as U.S. Pat. No. 5,084,588, involving the use of metal salts to neutralize the acid halide. U.S. Pat. No. 5,210,254 describes the addition of metal alkoxide species to neutralize the acid halide. The use of alkali metal salts, such as amides, imides, oxazolidinones, amines and sulfonamides, is proposed for removing acidic halides from organosilane compounds in U.S. Pat. Appl. Pub. No. US2005/0059835.

In preferred embodiments of the present invention, the dissolved residual chloride is removed by contacting the organosilicon composition with a stoichiometric excess of a basic chloride scavenger to cause at least a portion of the dissolved residual chloride to precipitate as a chloride salt. As used herein, the term "basic chloride scavenger" refers to a chemical substance which has a free pair of electrons available to bind a hydrogen ion and would therefore act as a "scavenger" by binding with the dissolved chloride as the hydrogen chloride salt, thus forming a solid salt precipitate. The term "basic impurity" as used herein refers to the presence of the basic chloride scavenger in the composition that is in excess of the amount of basic chloride scavenger needed to remove the dissolved residual chloride.

Preferred basic chloride scavengers suitable for use in the method of the present invention include ammonia, amine compounds, alcoholates, metal alkoxides, alkali metal salts, tetraethylene glycol di(2-ethylhexoate), metal salts of organic acids, epoxide-containing compounds, and mixtures thereof. Preferred epoxide-containing compounds include, for example, epoxidized linseed oil, epoxidized soybean oil, epoxidized α-olefins, epoxidized esters, glycidyl ethers, and mixtures thereof. In certain embodiments, the basic chloride scavenger is an alkali metal salt of an amide, an imide, an oxazolidinone, or a sulfonamide. In other embodiments, the basic chloride scavenger comprises an a salt of an organic acid such as, for example, sodium citrate.

In more preferred embodiments of the present invention, the basic chloride scavenger is ammonia or an amine. Preferred amines suitable for use in the method of the present invention include ammonia, urea, ethylenediamine (EDA), diethylenetriamine (DETA), triethylenetetramine (TETA), pyridine, triethylenediamine (TEDA), diethanolamine (DELA), triethanolamine (TELA), aminopropyldiethanolamine (APDEA), bis(p-aminocyclohexyl)methane (PACM), quinuclidine (QUIN), 3-Quinuclidinol, trimethylamine (TMA), tetramethylethylendiamine (TMEDA), tetramethyl-1,3-propanediamine (TMPDA), trimethylamine oxide (TMAO), N,N,N-tris(N',N'-dimethyl-3-aminopropyl)amine, 3,3'-bis(dimethylamino)-N-methyldipropylamine, choline hydroxide, 4-dimethylaminopyridine (DMAP), diphenylamine (DPA), tetraethylenepentamine (TEPA), and mixtures thereof. In the most preferred embodiments of the present invention, the basic chloride scavenger is ethylenediame, urea, ammonia, or mixtures thereof.

Step 130 of FIG. 1 can be carried out by any method known to those of ordinary skill in the art to effect a contact between the dissolved residual chloride and the basic chloride scavenger such that a reaction occurs to form the chloride salt precipitate. Examples of such methods include an in-situ chloride scavenger process wherein the basic chloride scavenger is present during the synthesis step, and as such is able to scavenge the chloride or hydrogen chloride through the precipitation of the corresponding chloride salt as it is produced during synthesis. This method has the additional potential benefit of facilitating the forward step of the synthesis reaction by driving the equilibrium to the right in favor of increased product formation through the rapid removal of one of the reaction products. Once the synthesis is complete the mixture is typically heated and or agitated/mixed to ensure the quantitative precipitation of the dissolved chloride. The chloride salt precipitate thus formed subsequently can be removed by any one of a variety of solids separation techniques such as, for example, filtration, decantation, centrifugation, or combinations of such techniques. Another method commonly practiced by those of ordinary skill in the art is to employ the basic chloride scavenger in a separate step after the completion of the primary synthesis reaction. In this case the initial synthesis mixture is typically contacted with the basic chloride scavenger in a separate step following the synthesis reaction, again for the purpose of removing the dissolved chloride from the desired product by forcing its precipitation as the chloride salt. The mixture would then be subjected to agitation/mixing for an appropriate length of time to ensure the complete precipitation of the chloride salt. The chloride salt precipitate thus formed is preferably subsequently removed by any one of a variety of solids separation techniques such as filtration, decantation, centrifugation, or combinations of such techniques.

Referring to step 140 of FIG. 1, the dissolved basic chloride scavenger is preferably at least partially removed to obtain a composition having a first concentration of dissolved basic chloride scavenger. As used herein, the phrase "a first concentration of dissolved basic chloride scavenger" means a concentration of basic chloride scavenger in the organosilicon composition that was added to react with and remove the dissolved residual chloride and/or a concentration of basic chloride scavenger in the organosilicon composition that remains in the composition after at least part of it has been removed. Since basic chloride scavengers can be difficult to remove after addition to the dissolved chloride-containing material, low levels of basic chloride scavengers often remain dissolved in solution as a basic impurity.

In one embodiment of the present invention, distillation can be employed to lower the concentration of dissolved residual chloride scavenger. For example, chloride scavengers according to the present invention may be selected based, in part, upon their volatility such that any residual unused scavenger or contaminant thereof can be readily separated by conventional distillation means. For example, a chloride scavenger according to the present invention can be one wherein the normal boiling point of the scavenger is sufficiently different than that of the DEMS, for example, such that the residual scavenger can be readily separated by distillation. For example, compounds such as diethylenetriamine (DETA) or triethylenetetramine (TETA) have normal boiling points of 207° C. and 277° C., respectively. These boiling points are substantially higher than the normal boiling point of DEMS (95° C.) and, therefore, allow for reasonably efficient separation by distillation. Another appropriate chloride scavenger is an alkyl substituted anilines such as, for example, 3,5-dimethylaniline, which has a normal boiling point of 217° C., or other similarly high boiling amines.

Alternatively, a solid scavenger material can be used, which is insoluble in DEMS, for example, such that any unused residual scavenger material can be readily separated from the DEMS by typical solids separations techniques such as filtration, centrifugation, etc. Another example is a preformed scavenger material, such as a pelletized or resin-bead material that can be employed in the form of a packed adsorbent bed. Even in the latter case there exists the possibility of a final distillation or filtration step to remove any contaminants which may have been leached from the solid adsorbent or resin material, which itself may have a detrimental impact on the quality of the DEMS material if not removed. Such precautions will ensure that the treated DEMS contains very low levels of both chloride and residual chloride scavenger.

In a preferred embodiment of the present invention, an organosilicon composition containing the dissolved residual chloride scavenger impurity is treated with an acid gas to remove the chloride scavenger which is basic. This process is detailed in U.S. patent application Ser. No. 11/753,073 filed on 24 May 2007, which is incorporated herein by reference. The method allows the an organosilicon composition such as, for example, an organosilicon composition comprising DEMS, to be treated (i.e, contacted) with an excess of basic chloride scavenger to ensure optimal removal of chlorides. The basic chloride scavenger itself can then be subsequently removed by contact with an excess of an acid gas such as, for example, $CO_2$, causing the precipitation of the corresponding carbonate salt. Any residual dissolved $CO_2$ is subsequently removed cleanly by flooding the composition with an inert gas such as, e.g., Ar, $N_2$ or He to produce the finish product which is substantially free of chlorides, nitrogen-containing scavengers and $CO_2$, and hence, is suitable for use as a source material for the manufacture of low dielectric constant materials for integrated circuits.

Contacting the organosilicon composition with an acid gas to form a precipitate comprising a salt of the acid gas can be carried out by any means known to those of ordinary skill in the art that will ensure a reaction between at least a portion of the basic chloride solution and the acid gas to form the corresponding insoluble salt (e.g., a carbonate salt when the acid gas is carbon dioxide). Such means include bubbling the acid gas from the bottom of a reactor or other vessel while the organosilicon composition is being agitated so that a high level of contact between the acid gas and the chloride scavenger is achieved.

According to the present invention, the first concentration of dissolved residual chloride and the first concentration of dissolved residual chloride scavenger are preferably determined based upon the solubility product constant of each component in the organosilicon composition, or $K_{sp}(os)$. "$K_{sp}(os)$" as used herein is defined as the equilibrium constant that applies to the dissolution of a slightly soluble compound. Although the solubility product constant, $K_{sp}$, is typically associated with an aqueous system, the general concept also applies to non-aqueous systems such as, for example, organosilicon solvent systems. Thus, for the purpose of the present invention, the solubility product constant $K_{sp}(os)$ refers to the solubility product constant within an organosilicon medium, namely the equilibrium constant that applies to the dissolution of a slightly soluble compound in an organosilicon solvent system.

According to the present invention, the first $K_{sp}(os)$ is, therefore, defined as the product of [the first concentration of the dissolved residual chloride in parts per million by weight]$^X$, wherein X is 1, 2, 3, or 4, and [the first concentration of the dissolved residual chloride scavenger in parts per million by weight]. X can be either 1, 2, 3, or 4 based upon whether the dissolved residual chloride scavenger forms a mono-, di-, tri, or tetrahydrochloride, respectively.

By determining the phase diagram of the dissolved residual chloride and the dissolved residual chloride scavenger according to the present invention, the upper limits of the first concentration of dissolved residual chloride and the first concentration of dissolved residual chloride scavenger can be obtained by employing the methods detailed above. Avoidance of these upper limits are necessary to ensure that precipitation of the solid chloride salt precipitate does not occur. Phase diagrams can be obtained by any means known to those skilled in the art. Preferably, such phase diagrams according to the present invention are obtained by titration. A typical titration method may involve preparing standards of known concentrations of chloride and scavenger in an organosilicon such as, for example, DEMS, and titrating until a precipitate appears. Such procedure is exemplified below employing ethylenediamine (EDA) as the dissolved residual chloride scavenger.

With an understanding of the upper limit, i.e., the limit beyond which a solid chloride precipitate will appear and the first $K_{sp}(os)$, the first concentration of dissolved residual chloride and the first concentration of dissolved residual chloride scavenger can be determined. To ensure that an organosilicon composition according to the present invention will not form a solid chloride salt, the first concentration of dissolved residual chloride is preferably less than the square root of the first $K_{sp}(os)$ when X is 1, less than cubed root of the first $K_{sp}(os)$ when X is 2, less than the fourth root of the first $K_{sp}(os)$ when X is 3, or less than the fifth root of the first $K_{sp}(os)$ when X is 4, and the first concentration of the dissolved residual chloride scavenger is less than the square root of the first $K_{sp}(os)$ when X is 1, less than the cubed root of the first $K_{sp}(os)$ when X is 2, less than the fourth root of the first $K_{sp}(os)$ when X is 3, or less than the fifth root of the first $K_{sp}(os)$ when X is 4.

More preferably, to ensure that an organosilicon composition according to the present invention will not form a solid chloride salt, each of the first concentration of dissolved residual chloride and the first concentration of the dissolved residual chloride scavenger is less than 95% of the square root of the first $K_{sp}(os)$ when X is 1, less than 95% of the cubed root of the first $K_{sp}(os)$ when X is 2, less than 95% of the fourth root of the first $K_{sp}(os)$ when X is 3, or less than 95% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 90% of the square root of the first $K_{sp}(os)$ when X is 1, less than 90% of the cubed root of the first $K_{sp}(os)$ when X is 2, less than 90% of the fourth root of the first $K_{sp}(os)$ when X is 3, or less than 90% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 85% of the square root of the first $K_{sp}(os)$ when X is 1, less than 85% of the cubed root of the first $K_{sp}(os)$ when X is 2, less than 85% of the fourth root of the first $K_{sp}(os)$ when X is 3, or less than 85% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 80% of the square root of the first $K_{sp}(os)$ when X is 1, less than 80% of the cubed root of the first $K_{sp}(os)$ when X is 2, less than 80% of the fourth root of the first $K_{sp}(os)$ when X is 3, or less than 80% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 75% of the square root of the first $K_{sp}(os)$ when X is 1, less than 75% of the cubed root of the first $K_{sp}(os)$ when X is 2, less than 75% of the fourth root of the first $K_{sp}(os)$ when X is 3, or less than 75% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 70% of the square root of the first $K_{sp}(os)$ when X is 1, less than 70% of the cubed root of the first $K_{sp}(os)$ when X is 2, less than 70% of the fourth root of the first $K_{sp}(os)$ when X is 3, or less than 70% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 65% of the square root of the first $K_{sp}(os)$ when X is 1, less than 65% of the cubed root of the first $K_{sp}(os)$ when X is 2, less than 65% of the fourth root of the first $K_{sp}(os)$ when X is 3, or less than 65% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 60% of the square root of the first $K_{sp}(os)$ when X is 1, less than 60% of the cubed root of the first $K_{sp}(os)$ when X is 2, less than 60% of the fourth root of the first $K_{sp}(os)$ when X is 3, or less than 60% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 55% of the square root of the first $K_{sp}(os)$ when X is 1, less than 55% of the cubed root of the first $K_{sp}(os)$ when X is 2, less than 55% of the fourth root of the first $K_{sp}(os)$ when X is 3, or less than 55% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 50% of the square root of the first $K_{sp}(os)$ when X is 1, less than 50% of the cubed root of the first $K_{sp}(os)$ when X is 2, less than 50% of the fourth root of the first $K_{sp}(os)$ when X is 3, or less than 50% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 45% of the square root of the first $K_{sp}(os)$ when X is 1, less than 45% of the cubed root of the first $K_{sp}(os)$ when X is 2, less than 45% of the fourth root of the first $K_{sp}(os)$ when X is 3, or less than 45% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 40% of the square root of the first $K_{sp}(os)$ when X is 1, less than 40% of the cubed root of the first $K_{sp}(os)$ when X is 2, less than 40% of the fourth root of the first $K_{sp}(os)$ when X is 3, or less than 40% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 35% of the square root of the first $K_{sp}(os)$ when X is 1, less than 35% of the cubed root of the first $K_{sp}(os)$ when X is 2, less than 35% of the fourth root of the first $K_{sp}(os)$ when X is 3, or less than 35% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 30% of the square root of the first $K_{sp}(os)$ when X is 1, less than 30% of the cubed root of the first $K_{sp}(os)$ when X is 2, less than 30% of the fourth root of the first $K_{sp}(os)$ when X is 3, or less than 30% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 25% of the square root of the first $K_{sp}(os)$ when X is 1, less than 25% of the cubed root of the first $K_{sp}(os)$ when X is 2, less than 25% of the fourth root of the first $K_{sp}(os)$ when X is 3, or less than 25% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 20% of the square root of the first $K_{sp}(os)$ when X is 1, less than 20% of the cubed root of the first $K_{sp}(os)$ when X is 2, less than 20% of the fourth root of the first $K_{sp}(os)$ when X is 3, or less than 20% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 15% of the square root of the first $K_{sp}(os)$ when X is 1, less than 15% of the cubed root of the first $K_{sp}(os)$ when X is 2, less than 15% of the fourth root of the first $K_{sp}(os)$ when X is 3, or less than 15% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 10% of the square root of the first $K_{sp}(os)$ when X is 1, less than 10% of the cubed root of the first $K_{sp}(os)$ when X is 2, less than 10% of the fourth root of the first $K_{sp}(os)$ when X is 3, or less than 10% of the fifth root of the first $K_{sp}(os)$ when X is 4. Still more preferably, to ensure that an organosilicon composition according to the present invention will not form a solid chloride salt, each of the first concentration of dissolved residual chloride and the first concentration of the dissolved residual chloride scavenger is less than 5% of the square root of the first $K_{sp}(os)$ when X is 1, less than 5% of the cubed root of the first $K_{sp}(os)$ when X is 2, less than 5% of the fourth root of the first $K_{sp}(os)$ when X is 3, or less than 5% of the fifth root of the first $K_{sp}(os)$ when X is 4. As used herein, the phrase "less than Z % of" wherein Z % represents a number percent such as, for example, 5%, 10%, 15%, 20%, etc., includes the number Z % and all numbers less than the number Z.

In preferred embodiments of the present invention, organosilicon compositions according to the present invention have a first concentration of dissolved residual chloride that is less than 20 ppm. In more preferred embodiments of the present invention, organosilicon compositions according to the present invention have a first concentration of dissolved residual chloride that is less than 10 ppm. In even more preferred embodiments, organosilicon compositions according to the present invention have a first concentration of dissolved residual chloride that is less than 5 ppm. In the most preferred embodiments of the present invention, organosilicon compositions according to the present invention have a first concentration of dissolved residual chloride that is less than 2 ppm.

In preferred embodiments of the present invention, organosilicon compositions according to the present invention have a first concentration of dissolved residual chloride scavenger that is less than 20 ppm. In more preferred embodiments of the present invention, organosilicon compositions according to the present invention have a first concentration of dissolved residual chloride scavenger that is less than 10 ppm. In even more preferred embodiments, organosilicon compositions according to the present invention have a first concentration of dissolved residual chloride scavenger that is less than 5 ppm. In the most preferred embodiments of the present invention, organosilicon compositions according to the present invention have a first concentration of dissolved residual chloride scavenger that is less than 2 ppm.

In a particularly preferred embodiment of the present invention, organosilicon compositions according to the present invention have a first concentration of dissolved residual chloride that is less than 2 ppm and a first concentration of dissolved residual chloride scavenger that is less than 5 ppm.

Such organosilicon compositions according to the present invention, will not form a solid chloride salt precipitate when it is mixed with either a second lot of organosilicon product by the same manufacturer or an organosilicon product of another manufacturer, each of which may have a second concentration of dissolved residual chloride, and a second concentration of dissolved residual chloride scavenger. This is of significant importance because during CVD processing it is not uncommon that different lots of organosilicon precursors such as, for example, DEMS, may be combined, such as when a partially empty container is back-filled with a second source container of organosilicon precursor, or when two different organosilicon precursor source containers are feeding a common manifold. For this reason, is very important that different lots of organosilicon precursor are mutually compatible upon mixing. For example, the precipitation of solids may occur if a sample of organosilicon precursor containing a substantial amount of dissolved residual chloride is combined with a second source of organosilicon precursor containing a substantial amount of dissolved residual basic chloride scavenger. Solids formation in this manner would pose potential problems such as restricting or blocking the flow of the liquid precursor, solids contamination of the liquid delivery or deposition hardware, and numerous potential performance and or quality issues associated with the deposited low dielectric films.

According to the present invention, a second organosilicon is an organosilicon that, although different (i.e., different manufacturing lot, different source) from the first organosilicon material, comprises substantially the same components as the first organosilicon material. For example, a second organosilicon comprising for example, DEMS, according to the present invention also comprises a second concentration of dissolved residual chloride, and a second concentration of dissolved residual chloride scavenger. Thus, the second organosilicon has a second $K_{sp}(os)$ defined as the product of [the second concentration of the dissolved residual chloride in parts per million by weight]$^X$, wherein X is 1, 2, 3, or 4, and [the second concentration of the dissolved residual chloride scavenger in parts per million by weight].

A second organosilicon according to the present invention may be, for example, the same organosilicon as the first organosilicon but from a different manufacturing lot, or it may be the same organosilicon as the first organosilicon but from a different manufacturer.

To ensure that a solid chloride salt will not precipitate when a first organosilicon comprising, for example, diethoxymethylsilane, a first concentration of dissolved residual chloride, and a first concentration of dissolved residual chloride scavenger is mixed with a second organosilicon comprising diethoxymethylsilane, a second concentration of dissolved residual chloride, and a second concentration of dissolved residual chloride scavenger, each of the second concentration of dissolved residual chloride and the second concentration of the dissolved residual chloride scavenger is preferably less than the square root of the first $K_{sp}(os)$ when X is 1, less than the cubed root of the first $K_{sp}(os)$ when X is 2, less than the fourth root of the first $K_{sp}(os)$ when X is 3, or less than the fifth root of the first $K_{sp}(os)$ when X is 4.

More preferably, to ensure that an organosilicon composition according to the present invention will not form a solid chloride salt, each of the second concentration of dissolved residual chloride and the second concentration of the dissolved residual chloride scavenger is less than 95% of the square root of the first $K_{sp}(os)$ when X is 1, less than 95% of the cubed root of the first $K_{sp}(os)$ when X is 2, less than 95% of the fourth root of the first $K_{sp}(os)$ when X is 3, or less than 95% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 90% of the square root of the first $K_{sp}(os)$ when X is 1, less than 90% of the cubed root of the first $K_{sp}(os)$ when X is 2, less than 90% of the fourth root of the first $K_{sp}(os)$ when X is 3, or less than 90% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 85% of the square root of the first $K_{sp}(os)$ when X is 1, less than 85% of the cubed root of the first $K_{sp}(os)$ when X is 2, less than 85% of the fourth root of the first $K_{sp}(os)$ when X is 3, or less than 85% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 80% of the square root of the first $K_{sp}(os)$ when X is 1, less than 80% of the cubed root of the first $K_{sp}(os)$ when X is 2, less than 80% of the fourth root of the first $K_{sp}(os)$ when X is 3, or less than 80% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 75% of the square root of the first $K_{sp}(os)$ when X is 1, less than 75% of the cubed root of the first $K_{sp}(os)$ when X is 2, less than 75% of the fourth root of the first $K_{sp}(os)$ when X is 3, or less than 75% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 70% of the square root of the first $K_{sp}(os)$ when X is 1, less than 70% of the cubed root of the first $K_{sp}(os)$ when X is 2, less than 70% of the fourth root of the first $K_{sp}(os)$ when X is 3, or less than 70% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 65% of the square root of the first $K_{sp}(os)$ when X is 1, less than 65% of the cubed root of the first $K_{sp}(os)$ when X is 2, less than 65% of the fourth root of the first $K_{sp}(os)$ when X is 3, or less than 65% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 60% of the square root of the first $K_{sp}(os)$ when X is 1, less than 60% of the cubed root of the first $K_{sp}(os)$ when X is 2, less than 60% of the fourth root of the first $K_{sp}(os)$ when X is 3, or less than 60% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 55% of the square root of the first $K_{sp}(os)$ when X is 1, less than 55% of the cubed root of the first $K_{sp}(os)$ when X is 2, less than 55% of the fourth root of the first $K_{sp}(os)$ when X is 3, or less than 55% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 50% of the square root of the first $K_{sp}(os)$ when X is 1, less than 50% of the cubed root of the first $K_{sp}(os)$ when X is 2, less than 50% of the fourth root of the first $K_{sp}(os)$ when X is 3, or less than 50% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 45% of the square root of the first $K_{sp}(os)$ when X is 1, less than 45% of the cubed root of the first $K_{sp}(os)$ when X is 2, less than 45% of the fourth root of the first $K_{sp}(os)$ when X is 3, or less than 45% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 40% of the square root of the first $K_{sp}(os)$ when X is 1, less than 40% of the cubed root of the first $K_{sp}(os)$ when X is 2, less than 40% of the fourth root of the first $K_{sp}(os)$ when X is 3, or less than 40% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 35% of the square root of the first $K_{sp}(os)$ when X is 1, less than 35% of the cubed root of the first $K_{sp}(os)$ when X is 2, less than 35% of the fourth root of the first $K_{sp}(os)$ when X is 3, or less than 35% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 30% of the square root of the first $K_{sp}(os)$ when X is 1, less than 30% of the cubed root of the first $K_{sp}(os)$ when X is 2, less than 30% of the fourth root of the first $K_{sp}(os)$ when X is 3, or less than 30% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 25% of the square root of the first $K_{sp}(os)$ when X is 1, less than 25% of the cubed root of the first $K_{sp}(os)$ when X is 2, less than 25% of the fourth root of the first $K_{sp}(os)$ when X is 3, or less than 25% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 20% of the square root of the first $K_{sp}(os)$ when X is 1, less than 20% of the cubed root of the first $K_{sp}(os)$ when X is 2, less than 20% of the fourth root of the first $K_{sp}(os)$ when X is 3, or less than 20% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 15% of the square root of the first $K_{sp}(os)$ when X is 1, less than 15% of the cubed root of the first $K_{sp}(os)$ when X is 2, less than 15% of the fourth root of the first $K_{sp}(os)$ when X is 3, or less than 15% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 10% of the square root of the first $K_{sp}(os)$ when X is 1, less than 10% of the cubed root of the first $K_{sp}(os)$ when X is 2, less than 10% of the fourth root of the first $K_{sp}(os)$ when X is 3, or less than 10% of the fifth root of the first $K_{sp}(os)$ when X is 4. Still more preferably, to ensure that an organosilicon composition according to the present invention will not form a solid chloride salt, each of the second concentration of dissolved residual chloride and the second concentration of the dissolved residual chloride scavenger is less than 5% of the square root of the first $K_{sp}(os)$ when X is 1, less than 5% of the cubed root of the first $K_{sp}(os)$ when X is 2, less than 5% of the fourth root of the first $K_{sp}(os)$ when X is 3, or less than 5% of the fifth root of the first $K_{sp}(os)$ when X is 4.

In preferred embodiments of the present invention, organosilicon compositions according to the present invention have a second concentration of dissolved residual chloride that is less than 20 ppm. In more preferred embodiments of the present invention, organosilicon compositions according to the present invention have a second concentration of dissolved residual chloride that is less than 10 ppm. In even more preferred embodiments, organosilicon compositions according to the present invention have a second concentration of dissolved residual chloride that is less than 5 ppm. In the most preferred embodiments of the present invention, organosilicon compositions according to the present invention have a second concentration of dissolved residual chloride that is less than 2 ppm.

In preferred embodiments of the present invention, organosilicon compositions according to the present invention have a second concentration of dissolved residual chloride scavenger that is less than 20 ppm. In more preferred embodiments of the present invention, organosilicon compositions according to the present invention have a second concentration of dissolved residual chloride scavenger that is less than 10 ppm. In even more preferred embodiments, organosilicon compositions according to the present invention have a second concentration of dissolved residual chloride scavenger that is less than 5 ppm. In the most preferred embodiments of the present invention, organosilicon compositions according to the present invention have a second concentration of dissolved residual chloride scavenger that is less than 2 ppm.

In a particularly preferred embodiment of the present invention, organosilicon compositions according to the present invention have a second concentration of dissolved residual chloride that is less than 2 ppm and a second concentration of dissolved residual chloride scavenger that is less than 5 ppm.

According to the present invention, the second concentration of dissolved residual chloride can be the same as or different from the first concentration of dissolved residual chloride and the second concentration of dissolved residual chloride scavenger can be the same as or different from the first concentration of dissolved residual chloride as long as each respective concentration is less than the square root of the first $K_{sp}(os)$. Such compositions according to the present invention will ensure that mixture will not produce a composition having chloride and scavenger concentrations above the upper solubility limit.

The present invention also provides a method for preventing solids formation in an organosilicon material employed in a chemical vapor deposition process, the method comprising the steps of providing an organosilicon material employed in a chemical vapor deposition process, the method comprising the steps of: providing an organosilicon composition comprising: at least one organosilicon selected from the group consisting of: an alkoxysilane and a carboxysilane; a first concentration of dissolved residual chloride; and a first concentration of dissolved residual chloride scavenger, wherein the organosilicon composition has a first $K_{sp}(os)$ defined as the product of [the first concentration of the dissolved residual chloride in parts per million by weight]$^X$, wherein X is 1, 2, 3, or 4 and [the first concentration of the dissolved residual chloride scavenger in parts per million by weight], wherein the first concentration of dissolved residual chloride is less than the square root of the first $K_{sp}(os)$ when X is 1, less than cubed root of the first $K_{sp}(os)$ when X is 2, less than the fourth root of the first $K_{sp}(os)$ when X is 3, or less than the fifth root of the first $K_{sp}(os)$ when X is 4, and the first concentration of the dissolved residual chloride scavenger is less than the square root of the first $K_{sp}(os)$ when X is 1, less than cubed root of the first $K_{sp}(os)$ when X is 2, less than the fourth root of the first $K_{sp}(os)$ when X is 3, or less than the fifth root of the first $K_{sp}(os)$ when X is 4; and providing a second organosilicon comprising at least one organosilicon selected from the group consisting of: an alkoxysilane and carboxysilane, a second concentration of dissolved residual chloride, and a second concentration of dissolved residual chloride scavenger, wherein the second organosilicon has a second $K_{sp}(os)$ defined as the product of [the second concentration of the dissolved residual chloride in parts per million by weight]$^X$, wherein X is 1, 2, 3, or 4, and [the second concentration of the dissolved residual chloride scavenger in parts per million by weight] and wherein each of the second concentration of dissolved residual chloride and the second concentration of the dissolved residual chloride scavenger is less than the square root of the first $K_{sp}(os)$ when X is 1, less than cubed root of the first $K_{sp}(os)$ when X is 2, less than the fourth root of the first $K_{sp}(os)$ when X is 3, or less than the fifth root of the first $K_{sp}(os)$ when X is 4.

The providing steps according to the method of the present invention include the sale of and/or the delivery of a composition according to the present invention.

Referring again to FIG. 1, for example, the present invention also provides a method for purifying an organosilicon composition comprising: at least one of an alkoxysilane and a carboxysilane; and dissolved residual chloride, the method comprising the steps of: contacting the organosilicon composition with a stoichiometric excess of a basic chloride scavenger to cause at least a portion of the dissolved residual chloride to precipitate as a chloride salt; removing the precipitated chloride salt from the organosilicon composition; contacting the organosilicon composition with an acid gas to form a precipitate comprising a salt of the acid gas upon reaction with the excess basic chloride scavenger; and removing the salt of the acid gas to form a purified organosilicon product.

Additional objects, advantages, and novel features of this invention will become apparent to those skilled in the art upon examination of the following examples thereof, which are not intended to be limiting.

EXAMPLES

Example 1

Preparation of Standards for Determination of Phase Diagram for EDA and HCl in DEMS Five samples of DEMS were prepared for use as standards or as components to prepare standard for the experiments described herein. (1) 1-1: 100 g of DEMS with 798 ppm EDA and 2.0 ppm chloride; (2) 1-2: 500 g of DEMS with no EDA and 2.0 ppm chloride; (3) 1-3: 150 g of DEMS with no EDA and 24 ppm chloride; (4) 1-4: 300 g of DEMS with no EDA and 1.4 ppm Cl−; and (5) 1-5: 200 g of DEMS with 310 ppm of EDA and 2.1 ppm of chloride.

The 53.2 ppm EDA in DEMS standard was made by combining 30.08 g of 1-1 with 421.01 g of 1-2. A DEMS sample with 202 ppm of EDA was then prepared by combining 320 g of the 53.2 ppm EDA sample with 80.28 g of 1-1 to form about 400 g of a sample with 202 ppm of EDA. The 17.0 ppm chloride in DEMS was prepared by combining 31.21 g of 1-4 with 69.45 g of 1-3. The 12.0 ppm chloride in DEMS was prepared by combining 53.19 g of 1-4 with 47.35 g of 1-3. The 9.0 ppm chloride in DEMS was prepared by combining 66.70 g of 1-4 with 34.00 g of 1-3.

Example 2

Precipitation Experiments

Figure 2:
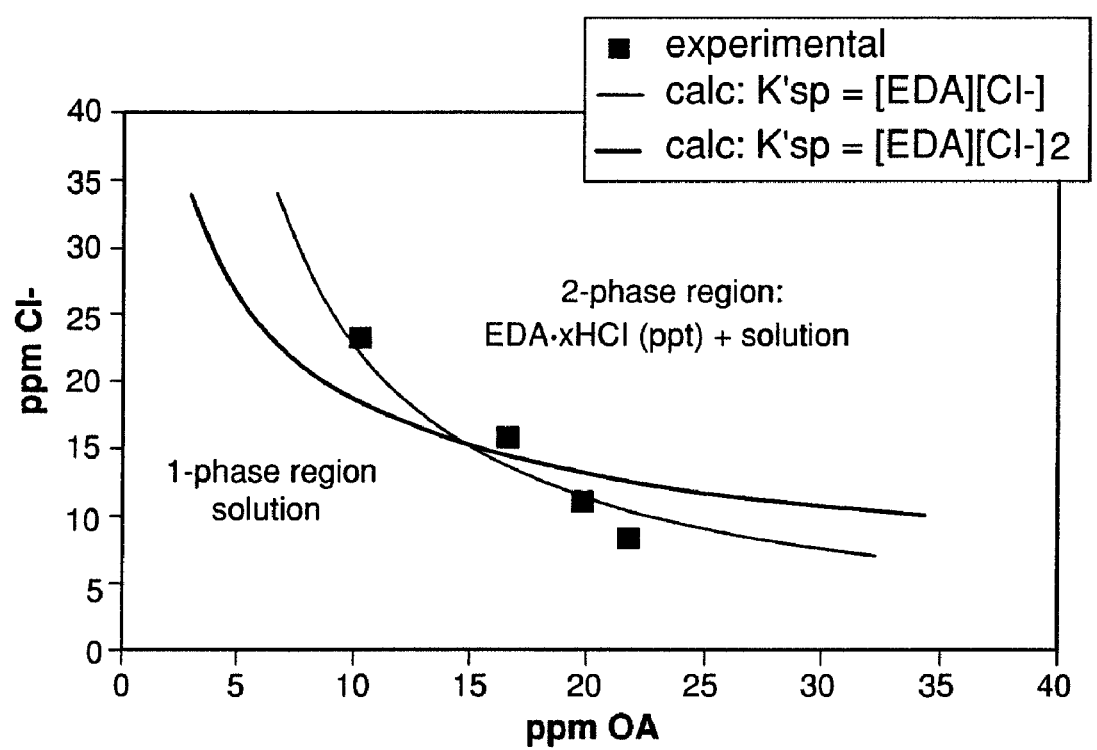
FIG. 2 is a phase diagram of a composition according to the present invention.

The standards described in Example #1 were used to carryout several precipitation experiments to define the phase diagram for EDA and HCl in DEMS. For each of these experiments, the EDA-containing DEMS was added drop-wise to the chloride-containing DEMS until the first sign of permanent visible turbidity was evident. The experiment was performed using a well lit dry box to improve visibility. A turbidity meter was used to verify the turbidity of the solution once the end-point was reached. A summary of the results is shown in Table 1. The phase diagram generated by these experiments is shown in FIG. 2.

Chloride level #1. The intent of this experiment was to determine the minimum amount of EDA that needed to be added to a DEMS solution containing 9.0 ppm chloride in order to cause the hydrochloride salt to precipitate. For this test 100.61 g of DEMS containing 9.0 ppm of chloride was placed in a 500 ml round-bottomed flask. A second sample of DEMS containing 202 ppm of EDA and 3.1 ppm of chloride was added drop-wise to this first DEMS sample while stirring rapidly to ensure homogeneity. Permanent turbidity was observed after the addition of 12.2 g of the EDA-containing solution. The net chloride content and EDA content of the composite solution was 8.4 ppm and 21.8 ppm, respectively.

Chloride level #2. The intent of this experiment was to determine the minimum amount of EDA needed to be added to a DEMS solution containing 12.0 ppm chloride in order to cause the hydrochloride salt to precipitate. For this test 100.59 g of DEMS containing 12.0 ppm of chloride was placed in a 500 ml round-bottomed flask. A second sample of DEMS containing 202 ppm of EDA and 3.1 ppm of chloride was added drop-wise to this first DEMS sample while stirring rapidly to ensure homogeneity. Permanent turbidity was observed after the addition of 10.9 g of the EDA-containing solution. The net chloride content and EDA content of the composite solution was 11.1 ppm and 19.8 ppm, respectively.

Chloride level #3. The intent of this experiment was to determine the minimum amount of EDA needed to be added to a DEMS solution containing 17.0 ppm chloride in order to cause the hydrochloride salt to precipitate. For this test 100.28 g of DEMS containing 17.0 ppm of chloride was placed in a 500 ml round-bottomed flask. A second sample of DEMS containing 202 ppm of EDA and 3.1 ppm of chloride was added drop-wise to this first DEMS sample while stirring rapidly to ensure homogeneity. Permanent turbidity was observed after the addition of 8.9 g of the EDA-containing solution. The net chloride content and EDA content of the composite solution was 15.9 ppm and 16.5 ppm, respectively.

Chloride level #4. The intent of this experiment was to determine the minimum amount of EDA needed to be added to a DEMS solution containing 24.0 ppm chloride in order to cause the hydrochloride salt to precipitate. For this test 99.83 g of DEMS containing 24.0 ppm of chloride was placed in a 500 ml round-bottomed flask. A second sample of DEMS containing 310 ppm of EDA and 2.2 ppm of chloride was added drop-wise to this first DEMS sample while stirring rapidly to ensure homogeneity. Permanent turbidity was observed after the addition of 3.4 g of the EDA-containing solution. The net chloride content and EDA content of the composite solution was 23.3 ppm and 10.2 ppm, respectively.

TABLE 1

Summary of experimental results for the determination of the phase diagram for EDA and HCl in DEMS.

| Chloride-Containing DEMS | | | EDA-Containing DEMS | | | Composite DEMS Sample | | |
|---|---|---|---|---|---|---|---|---|
| Total wt. (g) | EDA (ppm) | chloride (ppm) | total wt. (g) | EDA (ppm) | chloride (ppm) | total wt. (g) | EDA (ppm) | chloride (ppm) |
| 100.61 | 0 | 9.0 | 12.2 | 202 | 3.1 | 112.8 | 21.8 | 8.4 |
| 100.59 | 0 | 12.0 | 10.9 | 202 | 3.1 | 111.5 | 19.8 | 11.1 |
| 100.28 | 0 | 17.0 | 8.9 | 202 | 3.1 | 109.2 | 16.5 | 15.9 |
| 99.83 | 0 | 24.0 | 3.4 | 310 | 2.2 | 103.2 | 10.2 | 23.3 |

Referring to FIG. 2, the results of the chloride addition for the composite DEMS sample are plotted. Four data points were collected in order to generate the phase diagram depicted in FIG. 2. Each data point represents a specific EDA concentration and chloride concentration required to form a precipitate. To generate each data point, a first DEMS sample (noted in Table 1 as "EDA-Containing DEMS") with a predetermined concentration of chloride and EDA, was added drop-wise to a second DEMS sample (noted in Table 1 as "Chloride-Containing DEMS") also with a predetermined concentration of chloride and EDA. The drop-wise addition was terminated at the first sign of permanent visible turbidity. The four data points in FIG. 2 correspond to the EDA and chloride concentrations as listed in the "Composite DEMS Sample" section of Table 1. These EDA and chloride concentrations represent the weighted average of the EDA and chloride concentrations of each of the component DEMS samples.

The data used to generate the phase diagram are shown below in the Experimental section of Table 2. Two different solubility product constants were calculated for each data set of EDA and chloride concentration: $K'_{sp}$ and $K''_{sp}$. $K'_{sp}$ and $K''_{sp}$ are defined as the solubility product constants for the ethylenediamine monohydrochloride and ethylenediamine dihydrochloride salts, respectively, as follows:

$$K'_{sp}=[EDA][HCl]$$

$$K''_{sp}=[EDA][HCl]^2$$

From these four sets of data the average values were calculated for $K'_{sp}$ and $K''_{sp}$. In the second part of Table 2 below, the calculated EDA concentrations are shown using the average solubility product constants for the monohydrochloride salt and the dihydrochloride salt, assuming a given chloride concentration. These data were used to generate the calculated $K'_{sp}$ and $K''_{sp}$ curves depicted in the plot in FIG. 2.

TABLE 2

Experimental and calculated solubility product constant data used to generate plot in FIG. 2.

| Experimental | | | |
|---|---|---|---|
| [Cl-] | [EDA] | $K''_{sp}$ | $K'_{sp}$ |
| 23.3 | 10.2 | 5537 | 237.7 |
| 15.9 | 16.5 | 4171 | 262.4 |
| 11.1 | 19.8 | 2440 | 219.8 |

TABLE 2-continued

Experimental and calculated solubility product constant data used to generate plot in FIG. 2.

| 8.4 | 21.8 | 1538 | 183.1 |
|---|---|---|---|
| | Avg $K_{sp}$ | 3422 | 226 |

Calculated

| [Cl-] in ppm | [EDA] in ppm assuming $K''_{sp}$ | [EDA] in ppm assuming $K'_{sp}$ |
|---|---|---|
| 34 | 3.0 | 6.6 |
| 32 | 3.3 | 7.1 |
| 30 | 3.8 | 7.5 |
| 28 | 4.4 | 8.1 |
| 26 | 5.1 | 8.7 |
| 24 | 5.9 | 9.4 |
| 22 | 7.1 | 10.3 |
| 20 | 8.6 | 11.3 |
| 18 | 10.6 | 12.5 |
| 16 | 13.4 | 14.1 |
| 14 | 17.5 | 16.1 |
| 12 | 23.8 | 18.8 |
| 11 | 28.3 | 20.5 |
| 10 | 34.2 | 22.6 |
| 8 | 53.5 | 28.2 |
| 7 | 69.8 | 32.2 |

Figure 3:
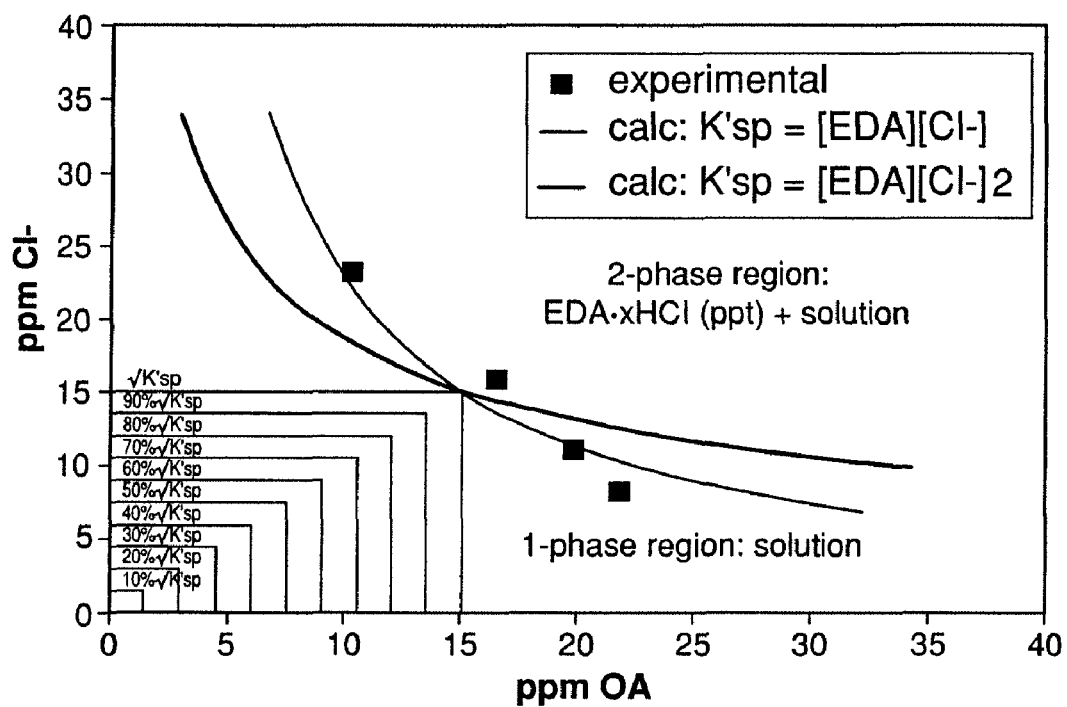
FIG. 3 is the phase diagram of FIG. 2 further illustrating preferred embodiments of the present invention.

FIG. 3 is the phase diagram of FIG. 2 further showing preferred embodiments according to the present invention. FIG. 3 illustrates embodiments such as, for example, wherein each of the first concentration of dissolved residual chloride and the first concentration of the dissolved residual chloride scavenger is less than 90%, 80%, 70%, 60%, 50%, 40%, 30%, 20%, and 10% of the square root of the first $K_{sp}$(os) when X is 1.

Example 3

Figure 4:
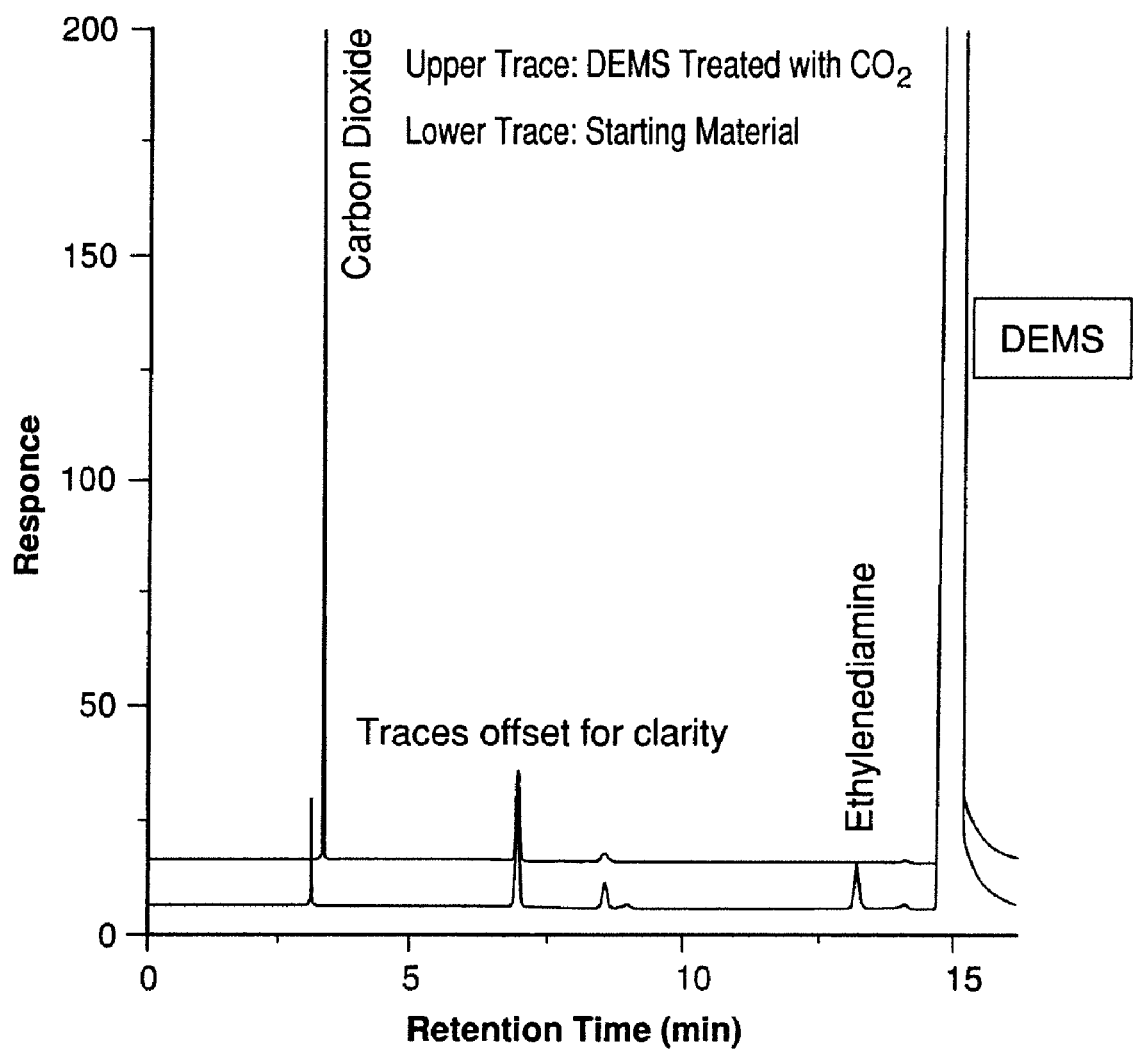
FIG. 4 is a comparative chromatogram that illustrates a feature of the present invention.

A 16 L sample of diethoxymethylsilane (DEMS) was analyzed by gas chromatography to contain 368 ppm of ethylenediamine (EDA). EDA had been used as a scavenger to remove the residual chloride following the synthesis of the DEMS. The residual EDA in the sample was present because a stoichiometric excess had been used to ensure optimal removal of the chloride species. The 16 L sample was transferred into a 20 L flask under inert gas conditions. The DEMS liquid was flooded with $CO_2$ gas for 90 minutes at a rate of about 2 to 3 liters per minute. An immediate precipitation of a milky white solid was observed upon the initial contact of $CO_2$ with the DEMS liquid. The 20 L flask was purged with $N_2$ gas to establish an inert atmosphere in the headspace above the liquid. The following day the solid was separated from the DEMS liquid by filtering the product through a 0.2 micron filter under inert gas conditions. The filtered liquid was evacuated, then back-filled with ambient pressure $N_2$. This step was repeated 2 more times to remove the dissolved $CO_2$ from the DEMS. Gas chromatography data comparing the DEMS before and after the $CO_2$ contact are shown in FIG. 4. Note that there is no EDA peak evident in the chromatogram of the sample that was contacted with $CO_2$. The EDA concentration dropped from an initial value of 368 ppm to <2 ppm EDA after the $CO_2$ contact. There is some $CO_2$ evident in this sample since the GC analysis shown in FIG. 4 was performed prior to the $N_2$ evacuation/back-fill step to remove the $CO_2$. Similar GC analysis of the $N_2$ treated sample showed no $CO_2$ present in the final sample. The data are summarized in Table 3.

Example 4

A 31 L (26 kg) sample of DEMS containing 28 ppm of EDA was placed in a 20 L flask. The DEMS was flooded with $CO_2$, filtered, and then flooded with $N_2$ gas in a manner similar to that described in the previous example. The final product had an undetectable amount of EDA (<2 ppm) as analyzed by GC. The data are summarized in Table 3.

Example 5

A 100 g sample of DEMS containing 573 ppm of EDA was transferred to a 500 ml quartz bubbler. The bubbler was equipped with inlet and outlet lines to allow gas purging. The inlet line consisted of a dip-tube that dropped to within 1/8" of the base of the bubbler. The bubbler was removed from the dry box and placed on a lab bench-top in a ventilated hood. The DEMS solution was purged with 300 sccm of $CO_2$ for 60 minutes. A cloudy precipitate was immediately evident upon initial contact of the $CO_2$ with the DEMS solution. The treated solution was allowed to sit overnight, resulting in a slightly opaque solution with a white precipitate at the bottom. The solid was removed by passing the solution through a 0.20 micrometer syringe filter. The filtered solution was placed into a clean bubbler. The bubbler was briefly evacuated for 10-15 seconds, followed by refilling with ambient pressure nitrogen. This evacuation-refill procedure was repeated a second time to ensure optimal $CO_2$ removal.

Small samples of the DEMS solution were set aside for EDA analysis as follows: (1) original DEMS that contained residual EDA; and (2) DEMS after $CO_2$ contact. Table 3 shows the EDA concentration of these samples. The original DEMS had 573 ppm EDA. The EDA level dropped about 100-fold to 5.4 ppm after the $CO_2$ flooding.

TABLE 3

Comparison of EDA concentration for $CO_2$ treatment of DEMS Before and After $CO_2$ Treatment.

| | | EDA concentration (ppm) | | |
|---|---|---|---|---|
| Example No. | organosilane | initial | after EDA spike | after $CO_2$ treatment |
| 1 | DEMS | 368 | N.A. | <2 |
| 2 | DEMS | 28 | N.A. | <2 |
| 3 | DEMS | 573 | N.A. | 5.4 |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

The invention claimed is:

1. A method for preventing solids formation in an organosilicon material employed in a chemical vapor deposition process, the method comprising the steps of:
   providing an organosilicon composition comprising:
   at least one organosilicon selected from the group consisting of: an alkoxysilane and a carboxysilane;
   a first concentration of dissolved residual chloride; and
   a first concentration of dissolved residual chloride scavenger, wherein the organosilicon composition has a first $K_{sp}(os)$ defined as the product of [upper limit of the first concentration of the dissolved residual chloride in parts per million by weight]$^X$, wherein X is 1, 2, 3, or 4 and [upper limit of the first concentration of the dissolved residual chloride scavenger in parts per million by weight] wherein the upper limits are limits beyond which a solid chloride precipitate will appear; and wherein the first concentration of dissolved residual chloride is less than the square root of the first Ksp(os) when X is 1, less than cubed root of the first Ksp(os) when X is 2, less than the fourth root of the first Ksp(os) when X is 3, or less than the fifth root of the first Ksp(os) when X is 4, and the first concentration of the dissolved residual chloride scavenger is less than the square root of the first Ksp(os) when X is 1, less than cubed root of the first Ksp(os) when X is 2, less than the fourth root of the first Ksp(os) when X is 3, or less than the fifth root of the first Ksp(os) when X is 4; and providing a second organosilicon comprising at least one organosilicon selected from the group consisting of: an alkoxysilane and carboxysilane, a second concentration of dissolved residual chloride, and a second concentration of dissolved residual chloride scavenger, wherein the second organosilicon has a second Ksp(os) defined as the product of [the second concentration of the dissolved residual chloride in parts per million by weight]X, wherein X is 1, 2, 3, or 4, and [the second concentration of the dissolved residual chloride scavenger in parts per million by weight] and wherein each of the second concentration of dissolved residual chloride and the second concentration of the dissolved residual chloride scavenger is less than the square root of the first Ksp(os) when X is 1, less than cubed root of the first Ksp(os) when X is 2, less than the fourth root of the first Ksp(os) when X is 3, or less than the fifth root of the first Ksp(os) when X is 4.

2. The method of claim 1 wherein each of the first and second organosilicon comprises at least one carboxysilane.

3. The method of claim 1 wherein each of the first and second organosilicon comprises at least one alkoxysilane.

4. The method of claim 3 wherein the alkoxysilane is diethoxymethylsilane.

5. The method of claim 4 wherein each of the first concentration of dissolved residual chloride and the first concentration of the dissolved residual chloride scavenger is less than 90% of the square root of the first Ksp(os) when X is 1, less than 90% of the cubed root of the first Ksp(os) when X is 2, less than 90% of the fourth root of the first Ksp(os) when X is 3, or less than 90% of the fifth root of the first Ksp(os) when X is 4.

6. The method of claim 5 wherein each of the second concentration of dissolved residual chloride and the second concentration of the dissolved residual chloride scavenger is less than 90% of the square root of the first Ksp(os) when X is 1, less than 90% of the cubed root of the first Ksp(os) when X is 2, less than 90% of the fourth root of the first Ksp(os) when X is 3, or less than 90% of the fifth root of the first Ksp(os) when X is 4.

7. The method of claim 4 wherein each of the first concentration of dissolved residual chloride and the first concentration of the dissolved residual chloride scavenger is less than 70% of the square root of the first Ksp(os) when X is 1, less than 70% of the cubed root of the first Ksp(os) when X is 2, less than 70% of the fourth root of the first Ksp(os) when X is 3, or less than 70% of the fifth root of the first Ksp(os) when X is 4.

8. The method of claim 7 wherein each of the second concentration of dissolved residual chloride and the second concentration of the dissolved residual chloride scavenger is less than 70% of the square root of the first Ksp(os) when X is 1, less than 70% of the cubed root of the first Ksp(os) when X is 2, less than 70% of the fourth root of the first Ksp(os) when X is 3, or less than 70% of the fifth root of the first Ksp(os) when X is 4.

9. The method of claim 4 wherein each of the first concentration of dissolved residual chloride and the first concentration of the dissolved residual chloride scavenger is less than 50% of the square root of the first Ksp(os) when X is 1, less than 50% of the cubed root of the first Ksp(os) when X is 2, less than 50% of the fourth root of the first Ksp(os) when X is 3, or less than 50% of the fifth root of the first Ksp(os) when X is 4.

10. The method of claim 9 wherein each of the second concentration of dissolved residual chloride and the second concentration of the dissolved residual chloride scavenger is less than 50% of the square root of the first Ksp(os) when X is 1, less than 50% of the cubed root of the first Ksp(os) when X is 2, less than 50% of the fourth root of the first Ksp(os) when X is 3, or less than 50% of the fifth root of the first Ksp(os) when X is 4.

11. The method of claim 4 wherein each of the first concentration of dissolved residual chloride and the first concentration of the dissolved residual chloride scavenger is less than 30% of the square root of the first Ksp(os) when X is 1, less than 30% of the cubed root of the first Ksp(os) when X is 2, less than 30% of the fourth root of the first Ksp(os) when X is 3, or less than 30% of the fifth root of the first Ksp(os) when X is 4.

12. The method of claim 11 wherein each of the second concentration of dissolved residual chloride and the second concentration of the dissolved residual chloride scavenger is less than 30% of the square root of the first Ksp(os) when X is 1, less than 30% of the cubed root of the first Ksp(os) when X is 2, less than 30% of the fourth root of the first Ksp(os) when X is 3, or less than 30% of the fifth root of the first Ksp(os) when X is 4.

13. The method of claim 4 wherein each of the first concentration of dissolved residual chloride and the first concentration of the dissolved residual chloride scavenger is less than 10% of the square root of the first Ksp(os) when X is 1, less than 10% of the cubed root of the first Ksp(os) when X is 2, less than 10% of the fourth root of the first Ksp(os) when X is 3, or less than 10% of the fifth root of the first Ksp(os) when X is 4.

14. The method of claim 13 wherein each of the second concentration of dissolved residual chloride and the second concentration of the dissolved residual chloride scavenger is less than 10% of the square root of the first Ksp(os) when X is 1, less than 10% of the cubed root of the first Ksp(os) when X is 2, less than 10% of the fourth root of the first Ksp(os) when X is 3, or less than 10% of the fifth root of the first Ksp(os) when X is 4.

\* \* \* \* \*